United States Patent
Choi et al.

(10) Patent No.: US 9,857,365 B2
(45) Date of Patent: Jan. 2, 2018

(54) FREEZE-DRIED CONJUGATE STRUCTURE FOR POINT-OF-CARE TESTING (POCT) IMMUNOCHROMATOGRAPHY, IMMUNOASSAY KIT COMPRISING THE SAME, AND METHOD FOR ANALYSIS USING THE KIT

(71) Applicant: SD BioSensor, Inc., Gyeonggi-do (KR)

(72) Inventors: Hyoung Gil Choi, Gyeonggi-do (KR);
Sung Yub Hong, Gyeonggi-do (KR);
Hee Young Hwang, Gyeonggi-do (KR);
Hyo Keun Lee, Gyeonggi-do (KR)

(73) Assignee: SD Biosensor, Inc., Gyeonggi-do (KR)

( * ) Notice: Subject to any disclaimer, the term of this patent is extended or adjusted under 35 U.S.C. 154(b) by 147 days.

(21) Appl. No.: 14/404,419

(22) PCT Filed: May 31, 2013

(86) PCT No.: PCT/KR2013/004843
§ 371 (c)(1),
(2) Date: Feb. 25, 2015

(87) PCT Pub. No.: WO2013/180533
PCT Pub. Date: Dec. 5, 2013

(65) Prior Publication Data
US 2015/0160203 A1    Jun. 11, 2015

(30) Foreign Application Priority Data
May 31, 2012    (KR) .................. 10-2012-0058708

(51) Int. Cl.
*G01N 33/53*    (2006.01)
*G01N 33/543*    (2006.01)
(Continued)

(52) U.S. Cl.
CPC ....... *G01N 33/5436* (2013.01); *G01N 33/532* (2013.01); *G01N 33/558* (2013.01);
(Continued)

(58) Field of Classification Search
CPC ............. G01N 33/532; G01N 33/5436; G01N 33/538; G01N 33/541; G01N 33/558;
(Continued)

(56) References Cited

U.S. PATENT DOCUMENTS 5,611,973 A    3/1997    Gurfein et al.
6,284,282 B1 *    9/2001    Maa ................. A61K 9/0075
424/45
(Continued)

FOREIGN PATENT DOCUMENTS

CN    102455361 A    5/2012
JP    H11201969 A    7/1999
(Continued)

OTHER PUBLICATIONS

Maa et al. Pharmaceutical Research, vol. 16, No. 2, 1999, pp. 249-254.*
(Continued)

*Primary Examiner* — Maureen Wallenhorst
(74) *Attorney, Agent, or Firm* — Mintz Levin Cohn Ferris Glovsky and Popeo, P.C.; Muriel Liberto, Esq.

(57) ABSTRACT

Described are immunoassay kits having a conjugate structure separate from an immunochromatographic strip in which the conjugate structure is freeze-dried with uniform droplet size, and related compositions and methods. The unique structure of the kits described here permits sample containing analyte to be reacted uniformly with the conjugate structure before being subjected to immunochromatography by application to the strip. This results in improved performance of the assay. In addition, the freeze-dried
(Continued)

conjugate structure can be stored without contamination and is easy to carry. In addition, the freeze-dried conjugate structure can be rapidly and uniformly dissolved so that it is immediately allowed to react with a mixture of a buffer and a sample, the reaction product then being analyzed by immunochromatography, making it suitable for use in point-of-care testing.

18 Claims, 6 Drawing Sheets

(51) Int. Cl.
*G01N 33/532* (2006.01)
*G01N 33/538* (2006.01)
*G01N 33/531* (2006.01)
*G01N 33/558* (2006.01)
*G01N 33/72* (2006.01)
*G01N 33/48* (2006.01)
*G01N 33/49* (2006.01)
*G01N 33/90* (2006.01)

(52) U.S. Cl.
CPC ........... *G01N 33/723* (2013.01); *G01N 33/49* (2013.01); *G01N 33/538* (2013.01); *G01N 33/90* (2013.01)

(58) Field of Classification Search
CPC ...... G01N 33/90; G01N 33/48; G01N 33/487; G01N 33/49; G01N 33/72; G01N 33/721; G01N 33/723
USPC ..... 436/63, 66, 67, 164, 165, 169, 180, 501, 436/514, 536, 540, 541; 422/400, 420, 422/421, 423, 424, 69, 549, 550, 558, 422/430; 435/7.1, 287.1, 287.2, 287.3, 435/287.7, 288.7; 530/391.1
See application file for complete search history.

(56) References Cited

U.S. PATENT DOCUMENTS

| | | | |
|---|---|---|---|
| 2001/0039059 A1 | 11/2001 | Freitag et al. | |
| 2006/0172435 A1* | 8/2006 | Cho ..................... | G01N 33/558 436/514 |
| 2007/0269839 A1* | 11/2007 | Goertz ............. | G01N 33/54313 435/7.32 |
| 2008/0090305 A1 | 4/2008 | Day et al. | |
| 2012/0282636 A1* | 11/2012 | Altschul .............. | G01N 33/558 435/7.92 |

FOREIGN PATENT DOCUMENTS

| | | |
|---|---|---|
| JP | 2002522767 A | 7/2002 |
| JP | 2010-256012 A | 11/2010 |
| KR | 10-0455298 B1 | 11/2004 |
| KR | 10-0506165 B1 | 7/2005 |
| KR | 10-0671825 B1 | 1/2007 |
| KR | 10-0747412 B1 | 8/2007 |
| WO | WO-94/0177 A1 | 1/1994 |
| WO | WO-02/14869 A2 | 2/2002 |
| WO | WO-02/14869 A3 | 2/2002 |
| WO | WO-2006/065118 A2 | 6/2006 |
| WO | WO-2006/065118 A3 | 6/2006 |
| WO | WO-2006/083367 A2 | 8/2006 |
| WO | WO-2006/083367 A3 | 8/2006 |
| WO | WO-2010/104937 A2 | 9/2010 |
| WO | WO-2010/104937 A3 | 9/2010 |
| WO | WO-2010132453 A2 | 11/2010 |
| WO | WO-2011059512 A1 | 5/2011 |

OTHER PUBLICATIONS

International Search Report Issued in PCT/KR2013/004843 dated Sep. 25, 2013.
Huang et al. Applications of Spray Freeze Drying in Processing of Pharmaceuticals and Extracts of Plant Resource, 2007, 27(S1): 143-146.

* cited by examiner

[FIG. 1]
conventional assay strip
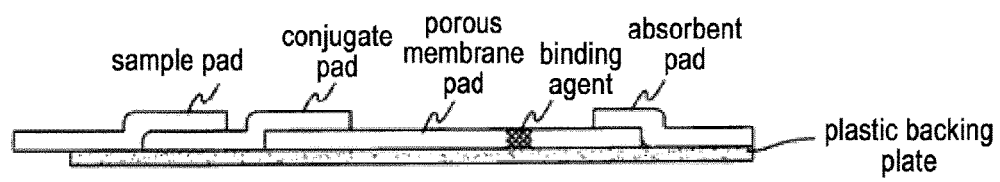
[FIG. 2]
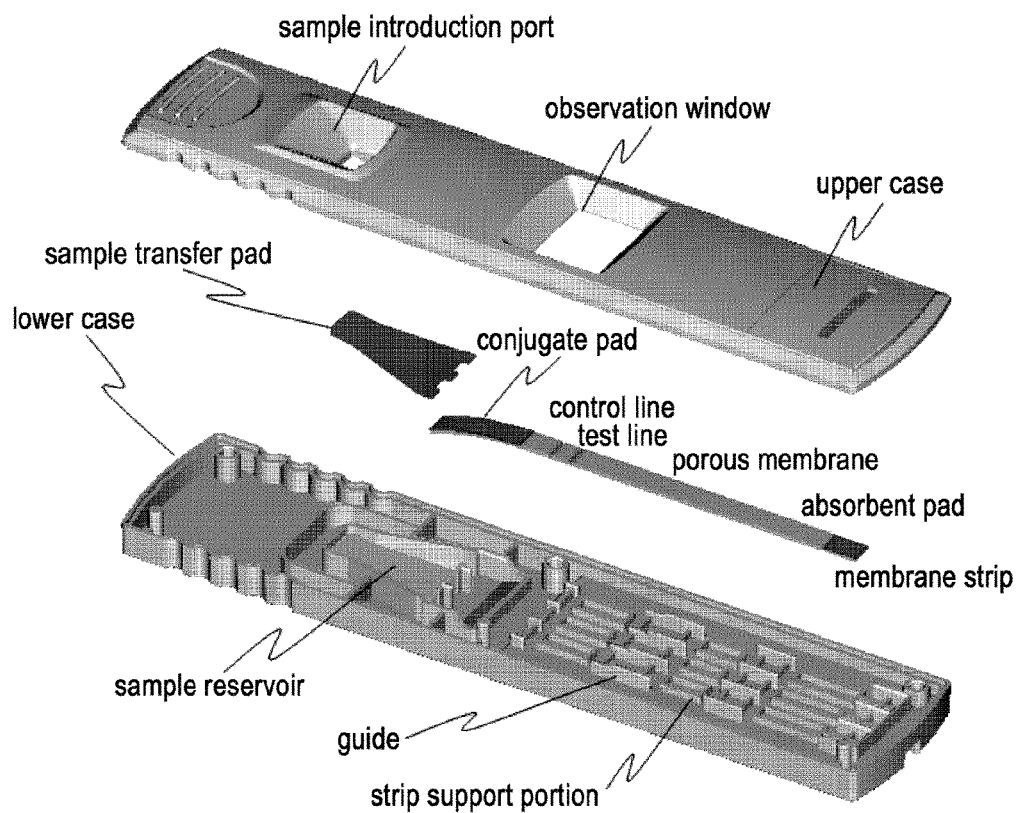

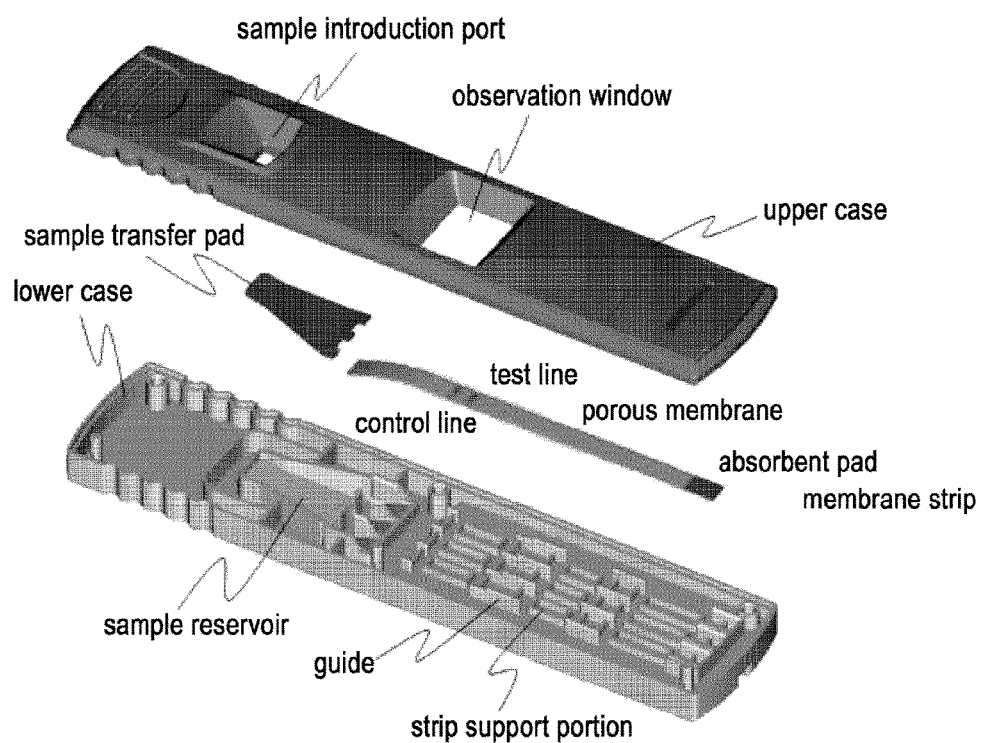
[FIG. 3]

[FIG. 4]
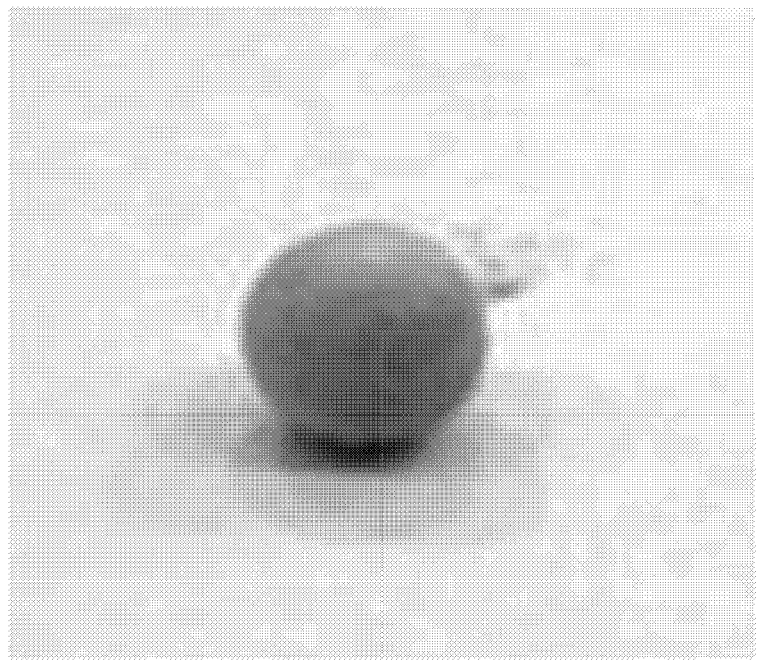

[FIG. 5A]
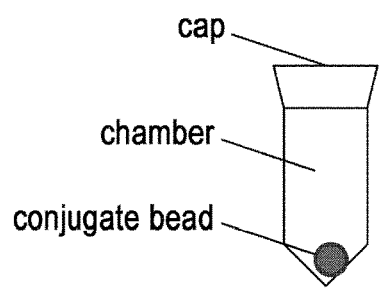
[FIG. 5B]
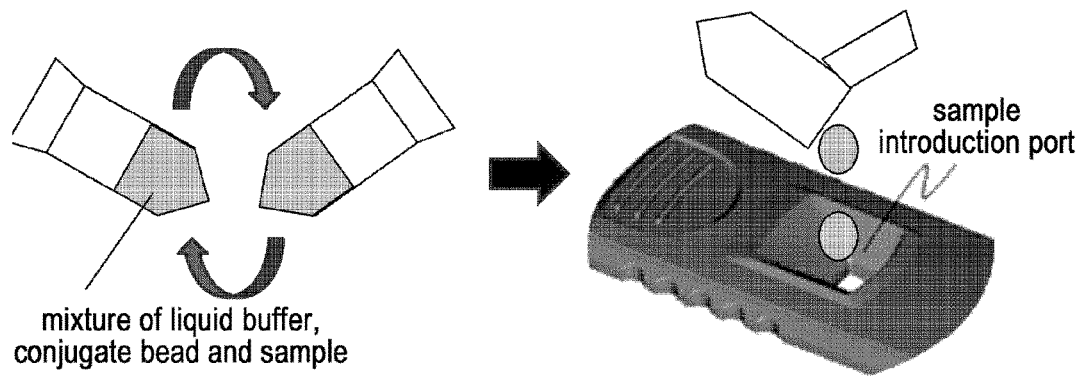

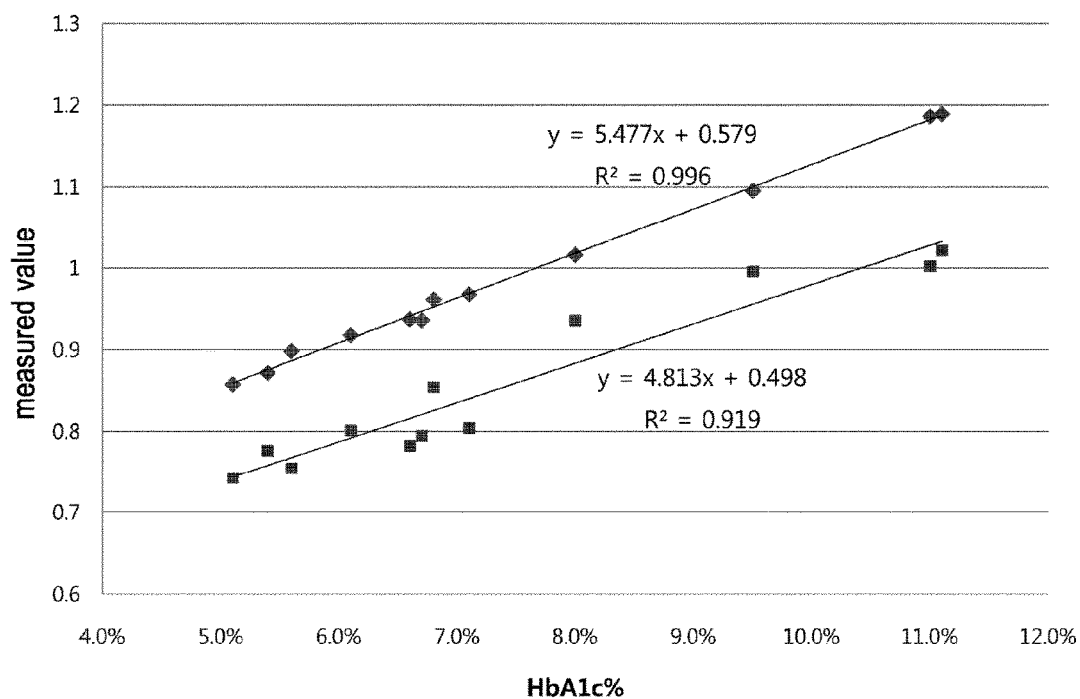
[FIG. 6]

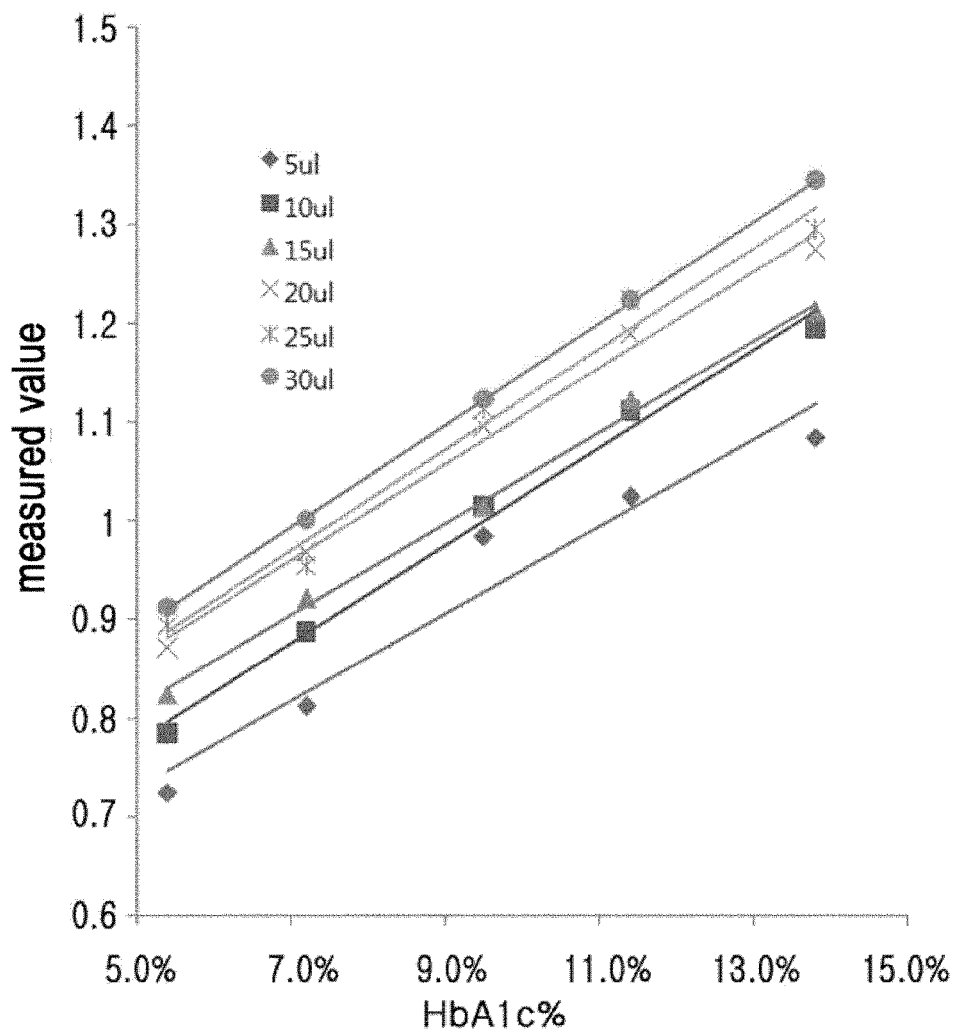
[FIG. 7]

FREEZE-DRIED CONJUGATE STRUCTURE FOR POINT-OF-CARE TESTING (POCT) IMMUNOCHROMATOGRAPHY, IMMUNOASSAY KIT COMPRISING THE SAME, AND METHOD FOR ANALYSIS USING THE KIT

TECHNICAL FIELD

The present invention relates to a freeze-dried conjugate structure for immunochromatography, an immunoassay kit comprising the freeze-dried conjugate structure and an immunochromatographic strip, and a method for qualitatively or quantitatively analyzing an analyte in a sample using the immunoassay kit.

BACKGROUND ART

An immunochromatographic assay, also known as a rapid test method, is a method capable of qualitatively and quantitatively analyzing a trace analyte within a short time using an antigen-antibody reaction and has been used to diagnose or detect various diseases and in various fields, including medical, agricultural, livestock, food, military and environmental fields. This immunochromatographic assay is typically performed using either an assay strip comprising a reaction material, which can change in response to the analyte to be detected, or an assay device comprising the assay strip mounted in a plastic case. FIG. 1 is a cross-sectional view of a conventional assay strip which is used in the immunochromatographic assay. As shown in FIG. 1, the conventional assay strip includes: a sample pad for receiving a liquid sample; a conjugate pad containing a conjugate, obtained by conjugating a label, which generates a signal that can be sensed visually or by a sensor to a ligand such as an antigen or an antibody; a porous membrane pad having immobilized thereon a binding substance (antibody or antigen) that binds specifically to an analyte in the sample and/or the conjugate; and an absorbent pad for finally receiving the liquid sample. These functional pads are connected to each other in the above order while partially overlapping each other, and attached to a solid support so that they are continuously arranged. In the case that the assay strip is used in a form being mounted in the plastic case, a sample introduction port for dropping the sample onto a position corresponding to the sample pad is formed on the case, and an observation window for observing assay results is formed at a position corresponding to the binding agent immobilized on the porous membrane pad. In the immunochromatographic assay that is performed using this assay strip, when a liquid sample is dropped onto the sample pad, it moves through the conjugate pad and the porous membrane pad by a capillary phenomenon, and is finally received in the absorbent pad. Herein, the conjugate in the conjugate pad also moves together with the liquid sample, and if the analyte to be detected is present in the sample, the conjugate will bind to the binding agent on the porous membrane pad through the analyte (generally referred to as a "sandwich reaction"), or the conjugate and the analyte competitively bind to the binding agent (generally referred to as "competition reaction"), and thus the presence of the analyte in the sample can be sensed visually or by a sensor.

However, this conventional assay strip has a problem in that the liquid sample that moves by a capillary phenomenon does not uniformly bind to the dry conjugate immobilized on the conjugate pad, and thus there may be a variation between the assay strips, suggesting that the accuracy and reproducibility of the quantitative analysis of the sample can be reduced.

In addition, in a method employing liquid reagents, which is frequently used in biochemical assays, the accuracy and reproducibility of sample analysis can be improved by mixing liquid reagents at a specific ratio in well-plate. However, when liquid reagents including an antibody and an antigen are stored for a long period of time, the affinity of antigen-antibody reactions will be reduced, or the antigen and the antibody will be denatured, suggesting that the liquid reagents are problematic in terms of stability. For this reason, liquid reagents can be cold- or freeze-stored in order to improve their long-term stability, but the cold- or freeze-stored liquid reagents are difficult to use in various measurement sites for point-of-care testing such as rapid testing.

Accordingly, the present inventors have made extensive efforts to increase the stability of a conjugate and improve the accuracy and reproducibility of sample analysis, and as a result, have developed a freeze-dried conjugate bead and a sample pretreatment device including the same, in which the freeze-dried conjugate bead has high long-term storage stability and is allowed to react uniformly with a sample in the sample pretreatment device to provide a reaction product, which has a size and concentration suitable for quantitative analysis and is subjected into an assay device, thereby completing the present invention.

DISCLOSURE

Technical Problem

It is an object of the present invention to provide a freeze-dried conjugate structure for immunochromatography, comprising a first conjugate comprising a first label for signal detection and a first ligand that reacts with an analyte, wherein the first label and the first ligand are physically or chemically linked to each other, and the conjugate structure is formed by rapidly freezing a dispersion, in which the first conjugate at a predetermined concentration is dispersed in a solvent, in the form of drops having a uniform volume, followed by freeze-drying, thereby removing the solvent, wherein the space occupied by the solvent in the freeze-dried drops forms a porous space by removing the solvent.

Another object of the present invention is to provide an immunoassay kit comprising the above freeze-dried conjugate structure and an immunochromatographic strip.

Still another object of the present invention provides a method for qualitatively or quantitatively analyzing an analyte in a sample using the above immunoassay kit, the method comprising: simultaneously or sequentially adding a buffer and a sample to a conjugate structure and simultaneously or sequentially performing the dissolution of the conjugate structure and a reaction between the conjugate and the sample; loading a material resulting from the preceding step onto an immunochromatographic strip and allowing the loaded material to migrate along the strip; and determining the presence or absence and intensity of a signal generated from a first label on a test line.

Technical Solution

In order to achieve the above objects, the present invention provides a freeze-dried conjugate structure for immunochromatography, comprising a first conjugate comprising a first label for signal detection and a first ligand that reacts with an analyte, wherein the first label and the first ligand are physically or chemically linked to each other, and the conjugate structure is formed by rapidly freezing a dispersion, in which the first conjugate at a predetermined concentration is dispersed in a solvent, in the form of drops having a uniform volume, followed by freeze-drying, thereby removing the solvent, wherein the space occupied by the solvent in the freeze-dried drops forms a porous space by removing the solvent.

As used herein, the term "immunochromatography" refers to an assay method that uses a combination of the immune reaction principle based on an antigen-antibody reaction and the chromatographic principle in which a sample and a reagent are moved along a medium by a mobile phase. Briefly, the antibody or antibody to be analyzed are dispensed and immobilized on a porous membrane in advance, and when blood sample migrates from one end of the membrane to the immobilized antibody or antigen, the reaction with the antigen or antibody in the sample is observed. In a general sense, the term "immune reaction" refers to an antigen-antibody reaction, but in a broader sense in the present invention, it is meant to include not only an antigen-antibody reaction, but also a reaction between a receptor and a ligand binding specifically thereto. Also, not limited thereto, it includes reactions between materials that specifically recognize each other, such as an enzyme-substrate reaction.

A label may be used so that the antigen-antibody reaction can be easily detected visually or using a sensor. In addition, a ligand capable of binding specifically to an analyte may be used in a state linked to the label so that the label can bind to the analyte to be detected. As used herein, the term "conjugate" refers to a conjugate of the label with the ligand. The label and the ligand can be physically or chemically linked to each other. Specifically, the label and the ligand can be linked to each other by passive adsorption, or the label can be modified to have a reactive group and can be covalently linked to the ligand, but is not limited thereto. In addition, linkage between the label and the ligand can be performed using any method known to those skilled in the art.

As used herein, the term "label" refers to a substance that generates a signal that can be sensed visually or using a sensor. Examples of the label that is used in the present invention include, but are not limited to, latex particles, gold particles, colored polystyrene microparticles, enzymes, fluorescent dyes, conductive polymers, or magnetic particles. In addition, the signal can be generated by the intrinsic characteristic (such as luminescence) of the label, or external stimulus such as fluorescence.

As used herein, the term "ligand" refers to a substance that binds specifically to a specific substance. For example, an antibody binding specifically to an antigen, or a ligand binding specifically to a specific receptor acts as a ligand to each other in a broader sense. In addition, any substance may be used as the ligand in the present invention, as long as it shows the above-described characteristics. In the context of the present invention, the term "ligand" refers to a substance that binds specifically to a specific substance as described above, unless it is specified as a ligand that binds specifically to a specific receptor.

The conjugate can be prepared by preparing a solution containing a predetermined concentration of the label and a solution containing a predetermined concentration of the ligand, mixing these solutions together, and allowing the mixed solution to react for a predetermined time. Herein, the concentrations of the solutions and the mixing ratio between the solutions can be determined in view of the binding ratio between the label and the ligand. The binding of the ligand to the label may be the binding of one ligand to one label, the binding of a plurality of ligands to one label, or the binding of a plurality of labels to one ligand. A specific binding ratio is not critical to the present invention, but is preferably maintained at a constant ratio. The binding ratio can change depending on the kinds of label and ligand and can be estimated in view of the relative size thereof and the number of binding sites. For example, when a latex bead having a size of several microns is used as the label and an antibody is used as the ligand, a plurality of antibodies can be bound to one latex bead. Preferably, in order to allow a uniform number of antibodies to bind to the surface of each latex bead, the concentrations and mixing ratio of the antibody and latex solutions can be controlled so that the antibodies are bound to the surface of the latex to saturate, but the scope of the present invention is not limited thereto.

As described above, a solution containing a predetermined concentration of the conjugate can be obtained by mixing solutions containing predetermined concentrations of the label and the ligand, respectively, and allowing the mixed solution to react. The conjugate solution is in the form of a dispersion in which the conjugate molecule is uniformly dispersed in a solution at a predetermined concentration.

The conjugate solution may further contain another conjugate molecule, which comprises a label for signal detection and a ligand that reacts with a reporter molecule immobilized on a control line, so that the conjugate molecule can be used as an internal control. The additional conjugate can be prepared as a uniform dispersion in the same manner as the method for preparing the above-described conjugate and may be mixed with the above-described conjugate solution. The label that is used in the additional conjugate molecule may be the same as or different from that in the above conjugate. The above terms and those for the internal control will be discussed in detail later.

In the present invention, for easy storage and uniform reactivity with a sample, the "freeze-dried conjugate structure" can be prepared by rapidly freezing a dispersion of the conjugate in the form of drops having a uniform volume, and freeze-drying the frozen drops. Specifically, a dispersion of conjugate molecules dispersed uniformly in a solvent at a predetermined concentration can be frozen by spraying drops of the dispersion, which have a uniform volume, so as to come into contact with an extremely-low-temperature liquid refrigerant. Herein, the drops of the dispersion are rapidly frozen to provide solid spheres having a uniform size. The extremely-low-temperature liquid refrigerant that is used in the present invention may be a liquid having an evaporation point between −270 and −180° C. For example, it may be liquid nitrogen, liquid helium, liquid oxygen, liquid hydrogen or the like and may be selected in view of cost and safety. Preferably, it may be liquid nitrogen or liquid helium, but is not limited thereto.

The immunochromatography in the present invention can be used in qualitative or quantitative analysis. In order to use the freeze-dried conjugate structure in quantitative analysis, each of the conjugate structures can be prepared to include a specific number of conjugate molecules. As described above, this preparation can be performed by preparing a uniform dispersion containing the conjugate at a predetermined concentration, and spraying drops of the dispersion, which have a uniform volume, into an extremely-low-temperature liquid refrigerant so as to be rapidly frozen. In order to spray the uniform conjugate dispersion in the form of drops having a uniform volume, a dispenser may be used. When the dispenser is used, the dispersion can be sprayed in the form of drops having a uniform volume, and the variation in the volume of the drops can be minimized. Herein, the volume of the dispersion drops being sprayed can be controlled by controlling the nozzle hole size and dispensing pressure of the dispenser. In addition, the size of the conjugate drops can be controlled depending on the composition and viscosity of the conjugate solution, the dropping rate and amount of the solution, and the surface tension of the drops. The solution drop may be a sphere having a volume of 5-30 µl and a diameter of 0.5-5 mm, but is not limited thereto.

The rapidly frozen conjugate structure can further be freeze-dried to provide a freeze-dried conjugate structure. In the freeze drying process, the solvent is removed from the frozen conjugate structure, and thus the structure becomes porous. The porous freeze-dried conjugate structure prepared as described above can be rapidly dissolved in a buffer so that it can react uniformly with a sample. The freeze drying process can be performed using a freeze dryer, and the cooling temperature in the freeze dryer may be −20° C. or lower. Preferably, the cooling temperature may be −40° C. or below, but is not limited thereto. The freeze drying time and temperature can be changed depending on the characteristics of the sample to be dried. The prepared freeze-dried conjugate structure has a porosity of 70-90% and can be completely dissolved in a buffer immediately or within 5 seconds after the start of the dissolution process.

In another aspect, the present invention provides an immunoassay kit comprising the above-described freeze-dried conjugate structure and an immunochromatographic strip.

As used herein, the term "immunoassay" refers to a method of detecting an analyte using a specific immune reaction such as an antigen-antibody reaction. Herein, immunochromatography can be performed using the chromatographic principle. Immunochromatographic analysis is performed while an analyte-containing sample is moved with a mobile phase through a medium by a capillary phenomenon. Thus, as the medium for immunochromatography, a strip can be prepared and used. The detailed elements and functions of this immunochromatographic strip will be described later.

As described above, immunochromatography is based on the chromatographic principle in which a mobile phase with an analyte moves along a medium. Thus, in order to perform an immunoassay using an immunochromatographic strip, a mobile phase for moving an analyte-containing sample along the strip is required. Thus, the immunoassay kit of the present invention may further include a buffer. The buffer functions not only as a mobile phase for moving a sample along the immunochromatographic strip, but also as a solvent for dissolving the conjugate. If necessary, it may also function as a diluent for diluting a sample. In addition, the immunoassay kit may further include a component for lysing blood cells such as red blood cells in order to analyze whole blood. As the buffer, a conventional buffer, such as 10 mM to 1 M phosphate buffered solution (PBS), a nonionic or amphoteric surfactant or a mixture thereof, may be used without limitation. The buffer can be suitably selected depending on the kind of desired reaction such as an antigen-antibody reaction.

Preferably, when the immunoassay kit of the present invention is used, a sample is allowed to react with a uniform solution of the freeze-dried conjugate structure in a buffer before the sample is injected into an immunochromatographic column in order to ensure a uniform reaction between the conjugate and the sample, and then may be analyzed using the assay strip.

For storage of the freeze-dried conjugate structure, it may be provided together with a chamber comprising a cap, which is provided for its dissolution in a buffer and its reaction with a sample. A buffer and a sample may be added directly to the freeze-dried conjugate structure kept in the chamber comprising the cap, so that the conjugate structure can be dissolved and can react uniformly with the sample. When the chamber is used, the freeze-dried conjugate structure can be stored in a state in which it is covered with the cap, the freeze-dried conjugate structure itself and/or a mixture thereof with a buffer and a sample can be stored without contamination. Preferably, the chamber may be conical in shape so that a reaction mixture solution can be easily loaded onto the strip using a device such as a pipette without being lost, but is not limited thereto.

Because the freeze-dried conjugate structure is one obtained by freezing the dispersion of the conjugate at a predetermined concentration as drops having a uniform volume, followed by freeze-drying the frozen drops, the structure has a constant content of the conjugate molecule, and thus is suitable for use in the quantitative analysis of an analyte.

In addition, the immunoassay kit may further comprise, as an internal control, a second freeze-dried conjugate structure comprising a second conjugate which comprises a second label for signal detection and a second ligand that reacts with a reporter molecule, in which the second freeze-dried conjugate structure is provided according to the same principle and preparation method as those for the above-described freeze-dried conjugate structure. As described above, the internal control can be provided by adding the second conjugate structure to the conjugate dispersion during the preparation of the freeze-dried conjugate structure to make a single structure. Alternatively, the second freeze-dried conjugate structure may be separately prepared using the same method as described above and may be added to a mixture of a sample and the conjugate. The internal control and the reporter molecule will be described later.

The immunochromatographic strip may comprise a porous membrane pad, which has formed thereon a test line for capturing an analyte in a sample, and an absorbent pad which is provided at one end of the porous membrane pad and serves to provide a driving force for transferring the analyte.

To detect an analyte in a sample, either a ligand capable of binding specifically to the analyte to selectively capture the analyte, or the same substance as the analyte, or an analogue thereof, which detect the analyte by inducing a competitive reaction with the analyte, is immobilized as a ligand on the porous membrane pad to form a "test line". On the test line of the immunochromatographic strip of the present invention, either a substance capable of binding to an analyte in a sample, or the same substance as the analyte, or an analogue thereof, which can induce a competitive reaction with the analyte, may be immobilized as a third ligand. The type of third ligand can be selected depending on the type of immunoassay used. The type of immunoassay will be described later. Like the ligand included in the conjugate, the second ligand, which reacts with the reporter molecule, and the third ligand that binds to an analyte in a sample, may be, for example, an antigen, an antibody, a receptor or a ligand that binds specifically to the receptor.

As a medium along which a mobile phase and a sample migrate, a porous membrane pad is used so that the mobile phase and the sample can be moved by a capillary phenomenon. At one end of the porous membrane pad, an absorbent pad that provides a driving force for transferring a sample is located. The absorbent pad may be located so that it partially overlaps the porous membrane pad. The membrane that is used in the present invention may be a nitrocellulose membrane, a glass fiber membrane, a polyethersulfone (PES) membrane, a cellulose membrane, a nylon membrane, or a combination of two or more thereof. Preferably, a nitrocellulose membrane having a pore size of 5-15 µm may be used in the present invention, but is not limited thereto.

The immunochromatographic strip may further comprise a solid backing plate. The solid backing plate may be made of a plastic material. When the strip is attached onto the solid backing plate, it can have increased durability and can be easily handled and stored. In addition, the solid backing plate makes it easy to mount the strip in an outer case. Examples of a plastic material that may be used for the solid backing plate include, but are not limited to, a polypropylene film, a polyester film, a polycarbonate film, an acrylic film and the like.

The immunochromatographic strip may be mounted in a case unit. A lower case may comprise a plurality of guides and/or strip support portions, which function to place and fix or press the immunochromatographic strip at a suitable position. An upper case may have guides and strip support portions at positions corresponding to the guides and strip support portions of the lower case. In other words, the guides and/or the strip support portions may be formed only in the lower case or formed in both the upper case and the lower case. The upper case may have a sample introduction port and an observation window for detecting a signal from the label at a position corresponding to the test line. The sample introduction port may be formed in the form of a hole or a slit at one end of the porous membrane, which is opposite to the absorbent pad, enough separated therefrom, with respect to the test line, so that a sample can migrate along the membrane. The observation window may be formed at a location corresponding to the test line of the porous membrane and/or a location including the test line and the control line (if formed) so as to have a size sufficient for observing the test line and/or the control line visually or using a sensor. The size and shape of the observation window are not limited, as long as the test line and/or the control line can be observed through the observation window.

The upper and lower cases may be made of a conventional plastic material, for example, polycarbonate or acrylonitrile butadiene styrene (ABS), but are not limited thereto. The upper and lower cases can be manufactured separately and coupled to each other through conventional means such as coupling grooves and coupling protrusions. In some cases, the upper and lower cases may be manufactured in an integral form.

When the immunoassay kit of the present invention is used, an analyte bound to the first conjugate, that is, an analyte bound to the first label through the first ligand, is captured on the test line by the third ligand binding specifically thereto, and the presence or absence, amount, or both, of the analyte in the sample can be determined by measuring a signal generated from the first label on the test line. In other words, the analyte can be qualitatively analyzed based on the presence or absence of a signal generated from the first label on the test line, and can also be quantitatively analyzed by measuring the intensity of a signal generated from the first label on the test line.

Thus, the immunochromatographic strip may further comprise, before or after the test line, a control line for determining whether the sample migrated. The control line may be formed by immobilizing a reporter molecule before or after the test line on the porous membrane at a suitable distance from the test line.

As used herein, the term "control line" refers to a portion that generates a constant signal regardless of the type of sample or the concentration of an analyte in a sample. The control line can be formed by a method similar to the method for forming the test line. For example, the control line can be formed by immobilizing a ligand substance that does not bind to the substance to be analyzed and, at the same time, can bind specifically to and capture the ligand of the second conjugate, which is included as an internal control in the mixture of the sample and the conjugate and is moved along the porous membrane together with the sample by a mobile phase, to emitting a constant signal regardless of the concentration and presence or absence of the analyte in the sample. A ligand that may be used for the control line is termed "reporter molecule" herein. Examples of a reporter molecule that is used in the present invention include anti-rabbit IgG, anti-chicken IgY, streptavidin, etc. The sizes and positions of the test line and the control line can be suitably selected depending on the antigen-antibody reaction used and the like. Whether the sample migrated can be determined based on the presence or absence of a signal emitted from the control line, and the quantitative analysis of the analyte can be performed by comparing the intensity of the signal of the test line with the intensity of the signal of the control line.

Immunoassays can be largely classified, according to principle, into two categories: a sandwich assay and a competitive or inhibition assay. In the case of the sandwich assay, the first ligand of the conjugate first immunologically reacts with an analyte in a sample to form an immune complex. The immune complex is moved along the immunochromatographic strip by a mobile phase and immune-specifically binds to and is captured by the test line having immobilized thereon a third ligand that binds specifically to the analyte. On the other hand, in the case of the competitive or inhibition assay, a third ligand that binds specifically to the first ligand of the conjugate is immobilized on the test line of the porous membrane. The third ligand may be the same substance as an analyte in a sample, or an analogue thereof, but any substance may be used as the third ligand without limitation, as long as it can bind to the first ligand competitively with the analyte. Because the intensity of a signal generated from the label of the conjugate captured by the test line through an immune reaction is proportional or inversely proportional to the concentration of the analyte in the sample, the presence or absence of the analyte can be qualitatively analyzed based on whether the signal is positive or negative, and the analyte can be quantitatively analyzed by comparing the intensity of the signal with the standard colorimetric system or the internal control.

In still another aspect, the present invention provides a method for qualitatively or quantitatively analyzing an analyte in a sample using the above immunoassay kit, the method comprising: simultaneously or sequentially adding a buffer and a sample to a conjugate structure and simultaneously or sequentially performing the dissolution of the conjugate structure and a reaction between the conjugate and the sample; loading a material resulting from the preceding step onto an immunochromatographic strip and allowing the loaded material to migrate along the strip; and determining the presence or absence and intensity of a signal generated from a first label on a test line.

The principle in which an analyte in a sample is qualitatively and/or quantitatively analyzed using the immunoassay kit of the present invention is as described above.

The immunoassay method of the present invention can be performed in the following manner. First, the conjugate structure is dissolved in a buffer, after which a sample is added to and uniformly mixed with the solution, and the mixture is allowed to react for a predetermined time. Alternatively, a buffer and a sample may be simultaneously added to the conjugate structure so that the conjugate structure is dissolved and, at the same time, can react with an analyte in the sample. Preferably, the conjugate structure is completely dissolved in a buffer to form a uniform dispersion of the conjugate molecules, and a sample is added to the dispersion so as to immunologically react with an analyte in the sample. However, the order in which the conjugate structure, buffer and the sample are mixed or reacted with each other is not limited, as long as the conjugate structure can be completely dissolved so that the conjugate molecules can be dissolved uniformly in the solution and react sufficiently with the sample to form an immune complex. Then, the solution containing the immune complex resulting from the dissolution and immune reaction step are loaded on the immunochromatographic strip and allowed to migrate along the strip, after which the qualitative or quantitative analysis of an analyte in the sample can be performed by determining the presence or absence and intensity of a signal generated from the first label on the test line.

As the solution containing the analyte that migrates along the porous membrane of the strip becomes more uniform, the migration speed of the mobile phase and the antigen-antibody reaction time become more constant, and thus the accuracy of sample analysis can be increased. Thus, the assay method of the present invention, which comprises mixing a sample with a uniform solution of the conjugate in a buffer, allowing the mixture to react sufficiently, loading the reaction mixture on the immunochromatographic strip and allowing the loaded mixture to migrate along the strip, is suitable for increasing the accuracy of analysis.

In an Example of the present invention, the assay method of the present invention and a conventional assay method employing an immunoassay strip further comprising a conjugate pad having a conjugate adsorbed thereon were performed, and the results of the assay methods were compared with each other. As a result, it was shown that more highly reproducible results could be obtained in the analysis of glycated hemoglobin using the method of the present invention (Table 1). Further, it was shown that the glycated hemoglobin concentration and the measured intensity of a signal in quantitative analysis were highly linearly correlated with each other (FIG. 6).

Examples of the sample that is used in the immunoassay of the present invention include all biological samples, including whole blood, blood cells, serum, plasma, bone marrow, sweat, urine, tears, saliva, skin, mucosa and hair, which are isolated from mammals, preferably humans. For example, the sample may be blood. The blood sample may be blood cell-free serum or plasma. When whole blood is used, a buffer containing a component capable of lysing blood cells may be used.

The immunoassay method of the present invention is useful for the analysis of blood glucose levels and the diagnosis of diseases using whole blood as a sample. Examples of the diseases include malaria antigen (Ag), AIDS, hepatitis C, hepatitis B, syphilis, gastric ulcer-causing microorganisms, cancer markers (AFP, PSA, CEA), tuberculosis, SAS, dengue fever, and leprosy. Preferably, the analyte may be glycated hemoglobin, but is not limited thereto.

According to a specific embodiment of the present invention, the concentration of glycated hemoglobin in blood can be measured by using blood as a sample, immobilizing anti-glycated hemoglobin antibody as the second ligand on the test line, and measuring the intensity of a signal generated from the label of the conjugate captured by the test line. For example, the measurement can be performed using a spectrophotometer as a sensor, but the detection method is not limited thereto. The concentration of glycated hemoglobin is generally expressed as the percentage of the glycated hemoglobin concentration relative to the total hemoglobin concentration. The percentage of the glycated hemoglobin concentration (HbA1c) relative to the total hemoglobin concentration (TotalHb) can be calculated using the following equation. When the percentage of the glycated hemoglobin concentration is 3-6.5%, the sample is judged to be normal, and when the percentage is 6.5-20%, the sample is diagnosed as diabetes.

$$HbA1c\,(\%) = \frac{HbA1c(\text{g/dL})}{TotalHb(\text{g/dL})} \times 100$$

In order to measure the concentrations of hemoglobin and glycated hemoglobin in human red blood cells, a step of lysing red blood cells is required. Like the conventional analysis of glycated hemoglobin, the assay method of the present invention may comprise a pretreatment step of lysing red blood cells. The lysis of red blood cells can be performed simultaneously with the conjugate-sample reaction by adding a blood cell lysis buffer to a liquid buffer that is used in the sample pretreatment step. Thus, the kit of the present invention is highly useful as a point-of-care testing kit.

Hereinafter, the present invention will be described in detail with reference to the accompanying drawings.

FIG. 3 is an exploded perspective view of an immunoassay device according to an embodiment of the present invention; FIG. 4 is a photograph of a freeze-dried conjugate according to the present invention; and FIG. 5 sequentially shows the steps of an immunoassay method according to the present invention. As shown in FIGS. 3 and 5, the immunoassay device according to the present invention comprises: at least one membrane strip comprising a porous membrane having formed thereon a test line which has immobilized thereon a binding agent (antigen, antibody or ligand) that binds to a detectable analyte in a sample and/or a conjugate by an immune specific reaction, that is, an antigen-antibody reaction, in order to qualitatively or quantitatively analyze the analyte by an immunochromatographic assay; an upper case covering the upper part of the membrane strip and having a sample introduction port and an observation window; a lower case covering the lower part of the membrane strip and having a sample reservoir; and a sample pretreatment device (FIG. 5) which contains a freeze-dried conjugate comprising the conjugate and serves to mix the sample, a liquid buffer and the conjugate with each other and introduce the mixture into the sample reservoir. Alternatively, the immunoassay device may consist only of the membrane strip and the sample pretreatment device.

Advantageous Effects

Because a sample is subjected to immunochromatography after reacting uniformly with a freeze-dried conjugate structure separately prepared according to the present invention externally, quantitative analysis can be performed with high reproducibility and linearity depending on a concentration compared to a conventional assay method which is performed using an immunochromatographic strip comprising a conjugate pad prepared by adsorbing a conjugate.

In addition, the freeze-dried conjugate structure of the present invention can be provided in a state in which it is received in a chamber additionally comprising a cap. Thus, it can be stored without contamination and is easy to carry. In addition, the freeze-dried conjugate structure can be rapidly and uniformly dissolved so that it is immediately allowed to react with a mixture of a buffer and a sample and the reaction product can be analyzed by an immunoassay kit. Thus, it is suitable for use in point-of-care testing.

DESCRIPTION OF DRAWINGS

FIG. 1 is a cross-sectional view of an assay strip which is used in a conventional immunochromatographic assay.

FIG. 2 is an exploded perspective view of a conventional immunoassay device.

FIG. 3 is an exploded perspective view of an immunoassay device according to an embodiment of the present invention.

FIG. 4 shows the shape of a freeze-dried conjugate bead according to an embodiment of the present invention.

FIG. 5 shows a perspective view of a sample pretreatment device and an immunoassay method according to an embodiment of the present invention. Specifically, FIG. 5(A) shows a sample pretreatment device, which is a chamber equipped with a cap and containing a freeze-dried conjugate bead. FIG. 5(B) shows an immunoassay method employing the sample pretreatment device.

FIG. 6 shows a comparison of the results of quantitative analysis of glycated hemoglobin, performed using immunoassay devices according to the Example of the present invention and the Comparative Example. The diamonds indicate the measurement values obtained by the immunoassay device according to the Example of the present invention, and the squares indicate the measurement values obtained by a conventional immunoassay device according to the Comparative Example.

FIG. 7 shows changes of measured values for glycated hemoglobin depending on a volume of a freeze-dried conjugate bead according to an embodiment of the present invention.

MODE FOR INVENTION

Hereinafter, the present invention will be described in further detail with reference to examples. It is to be understood, however, that these examples are for illustrative purposes only and are not intended to limit the scope of the present invention.

Example 1: Analysis of Glycated Hemoglobin Using Freeze-Dried Conjugate Bead A. Preparation of Antibody-Immobilized Nitrocellulose Pad A monoclonal antibody to glycated hemoglobin was diluted in 0.1 M phosphate buffered solution (PBS) at a concentration of 1 mg/ml, and then sprayed onto the test line position of a nitrocellulose pad (width: 25 mm; pore size: 10-12 µm) using a dispenser. Meanwhile, anti-rabbit immunoglobulin G antibody obtained by inoculating rabbit immunoglobulin G into a mouse was diluted in 0.1 M PBS at a concentration of 1 mg/ml, sprayed onto the control line position of the nitrocellulose pad and dried in an incubator at 37° C. so as to be immobilized. On the portion excluding the antibody-immobilized portion of the nitrocellulose pad, a PBS containing 0.05 wt % bovine serum albumin, 4 wt % sucrose and 0.0625 wt % ionic surfactant was sprayed to block and dried in an incubator at 30° C. for 60-120 minutes. The resulting nitrocellulose pad was attached to a polypropylene backing plate having an adhesive applied thereon, and then an absorbent pad (Millipore, USA) was attached onto the nitrocellulose pad so that it overlapped by 1 mm.

B. Preparation of Freeze-Dried Conjugate Beads Comprising Antibody-Latex Conjugate A conjugate solution was prepared in the following manner. First, each of anti-glycated hemoglobin monoclonal antibody and rabbit immunoglobulin G was added at various concentrations to ml of an aqueous solution of latex in 0.1 M MES (2-(N-morpholino)ethanesulfonic acid) buffer (pH 6.0), and then allowed to react in an incubator at 37° C. for 1 hour. Each of the resulting conjugate solutions was centrifuged once at 12,000 rpm, and the supernatant was removed, thus removing unreacted antibody. To the remaining material, a buffer containing 1 wt % bovine serum albumin was added and allowed to react for 24 hours, so that the unreacted latex surface was blocked with the bovine serum albumin. The buffer used was 0.1 M PBS containing, in addition to 1 wt % bovine serum albumin, 0.5 wt % sucrose, 1 wt % PEG (polyethylene glycol), 1 wt % PVA (polyvinyl alcohol) and the like.

The resulting conjugate-containing solution was added dropwise to liquid nitrogen using a dispenser in the form of a drop having a volume of 20 µl so that it was rapidly frozen. This rapid freezing process was repeated to obtain conjugate beads which were then freeze-dried in a freeze dryer for 20 hours.

C. Manufacture of Immunoassay Device

The strip prepared in step A was mounted in a lower case, and then covered with an upper cover, thereby manufacturing an immunoassay strip device (FIG. 3) according to an embodiment of the present invention. Each of the freeze-dried conjugate beads (FIG. 4) prepared in step B was placed in a pretreatment device (FIG. 5) which was then covered with a cap. The manufactured immunoassay strip device and the pretreatment device were dehumidified, sealed, packaged in single pouches and stored.

Comparative Example 1: Preparation of Conventional Assay Strip Comprising Conjugate Pad A. Preparation of Antibody-Immobilized Nitrocellulose Pad An antibody-immobilized nitrocellulose pad was prepared in the same manner as described in step A of Example 1.

B. Preparation of Antibody-Latex Conjugate Pad

An antibody-latex conjugate solution was prepared in the same manner as described in step B of Example 1. The prepared conjugate solution was applied to the glass fiber pad shown in FIG. 1 at a density of 10 µl/25 mm² using a dispenser. The pad having the antibody-latex conjugate applied thereto was frozen rapidly with liquid nitrogen, and then dried in a freeze dryer for 20 hours, and the dried pad was cut to a size of 7 mm×30 mm.

The resulting conjugate pad was attached to a polypropylene backing plate having an adhesive applied thereon so that 1 mm of the conjugate pad overlapped the lower side of the nitrocellulose pad attached to the backing plate.

C. Manufacture of Immunoassay Device

Pads, including the nitrocellulose pad and conjugate pad prepared in steps A and B of Comparative Example 1, were arranged as shown in FIG. 1 so that they overlapped each other. The arrangement was mounted in a lower case and covered with an upper case, thereby manufacturing an immunoassay strip device (FIG. 2) according to the Comparative Example. The manufactured immunoassay strip device was dehumidified, sealed, packaged in a single pouch and stored.

Test Example 1: Comparison of Measurement Performance for Glycated Hemoglobin Between Assay Strips Employing Conjugate Pad and Freeze-Dried Conjugate Bead, Respectively In order to compare performance between the assay strips prepared in Example 1 and Comparative Example 1, the level of glycated hemoglobin in 10 blood samples was measured 10 times for each sample using each assay strip. Also, the level of glycated hemoglobin in each of the 10 blood samples used in the above measurement was measured using an automated testing system (Variant II Turbo; Bio-Rad Laboratories, Hervules, Calif., USA) and compared with the measurement results obtained using the assay strips prepared in Examples 1 and Comparative Example 1. The measurement results obtained using the prepared assay strips were expressed as numerical values using a spectrophotometer capable of measuring the intensity of light in the specific regions of the membrane, including the test line and the control line. From the numerical values measured in the test line and the control line by the spectrophotometer, the glycated hemoglobin level (HbA1c %) was calculated. The results of the calculation are shown in Table 1 below.

TABLE 1

Comparison of performance for measurement of glycated hemoglobin

| Sample No. | Automated testing system Average of measurements | Example Average of measurements | CV % | Comparative Example Average of measurements | CV % |
|---|---|---|---|---|---|
| Sample 1 | 5.6% | 5.4% | 2.3 | 5.2% | 9.7 |
| Sample 2 | 6.5% | 6.6% | 3.1 | 5.6% | 9.5 |
| Sample 3 | 7.4% | 7.2% | 3.4 | 6.5% | 7.6 |
| Sample 4 | 7.9% | 8.0% | 2.5 | 8.3% | 5.0 |
| Sample 5 | 8.7% | 8.8% | 3.8 | 8.5% | 5.5 |
| Sample 6 | 9.5% | 9.3% | 2.6 | 9.7% | 3.0 |
| Sample 7 | 5.4% | 5.4% | 2.9 | 5.8% | 4.8 |
| Sample 8 | 6.1% | 6.1% | 2.6 | 6.7% | 2.4 |
| Sample 9 | 7.2% | 7.1% | 3.2 | 7.6% | 5.1 |
| Sample 10 | 7.9% | 8.1% | 3.2 | 7.6% | 5.9 |

As can be seen in Table 1 above, the measurement values obtained using the assay strip prepared in Example 1 had high reproducibility (low coefficient of variation; CV %) compared to the measurement values obtained using the assay strip prepared in Comparative Example 1. In addition, when the measurement values were compared with the measurement values obtained by the automated testing system, it could be seen that the measurement values obtained using the assay strip of Example 1 had a low variation compared to the measurement values obtained using the assay strip of Comparative Example 1. In other words, it was shown that the use of the method for measuring glycated hemoglobin using the assay strip of the present invention showed high accuracy and reproducibility compared to the use of the conventional method.

Test Example 2: Comparison of the Ability to Quantitatively Analyzing Glycated Hemoglobin Between Immunoassay Devices Employing Conjugate Pad and Freeze-Dried Conjugate Bead, Respectively In order to compare the ability to quantitative analysis between the immunoassay devices manufactured in Example 1 and Comparative Example 1, 12 blood samples containing various concentrations of glycated hemoglobin were analyzed. In addition, the level of glycated hemoglobin in each of the 12 samples used in the above analysis was measured using an automated testing system (Variant II; Bio-Rad Laboratories, Inc) as described in Test Example 1, and its relationship with the glycated hemoglobin concentration was analyzed. The results of the analysis are shown in FIG. 6. In FIG. 6, the diamonds indicate the signal values (intensities) measured by the immunoassay device manufactured in Example 1 of the present invention, and the squares indicate the signal values (intensities) measured by the immunoassay device manufactured in Comparative Example 1. As can be seen in FIG. 6, the measurement values obtained by the immunoassay device of the present invention were proportional to the concentration of glycated hemoglobin and had high linearity over a wide concentration range including a range in which diabetes can be diagnosed ($R^2=0.996$). On the other hand, the measurement values obtained by the immunoassay device of Comparative Example 1, similar to a conventional immunoassay device, showed a tendency to be generally proportional to the concentration of glycated hemoglobin, but had low linearity ($R^2=0.919$), and particularly showed an unreliable low linearity for the samples containing glycated hemoglobin at a concentration of 5-8%, which includes 6.5%, a standard for diagnosing diabetes ($R^2=0.747$; data not shown). The glycated hemoglobin concentrations and measurement values for the samples used in the concentration dependence test are summarized in Table 2 below.

TABLE 2

Comparison of the ability to quantitatively analyze glycated hemoglobin

| Sample No. | HbA1c | A (◆) | B (■) |
|---|---|---|---|
| Sample 1 | 5.1% | 0.85709 | 0.74213 |
| Sample 2 | 5.4% | 0.87160 | 0.77635 |
| Sample 3 | 6.6% | 0.93709 | 0.78221 |
| Sample 4 | 6.7% | 0.93586 | 0.79454 |
| Sample 5 | 7.1% | 0.96748 | 0.80414 |
| Sample 6 | 8.0% | 1.01602 | 0.93555 |
| Sample 7 | 9.5% | 1.09534 | 0.99538 |
| Sample 8 | 11.1% | 1.18901 | 1.02154 |
| Sample 9 | 11.0% | 1.18645 | 1.00212 |
| Sample 10 | 5.6% | 0.89845 | 0.75455 |

TABLE 2-continued

Comparison of the ability to quantitatively
analyze glycated hemoglobin

| Sample No. | HbA1c | A (♦) | B (■) |
|---|---|---|---|
| Sample 11 | 6.1% | 0.91795 | 0.80114 |
| Sample 12 | 6.8% | 0.96111 | 0.85412 |

A: immunoassay device (Example 1) of the present invention; B: conventional immunoassay device (Comparative Example 1).

Test Example 3: Change in Glycated Hemoglobin Measurement Value Depending on the Volume of the Drop of a Freeze-Dried Conjugate In order to confirm that in the preparation of a freeze-dried conjugate structure uniformity in the volume of drops is closely related to quantitative analysis ability, six different freeze-dried conjugate structures, each being made with drops having a uniform volume of 5 μl, 10 μl, 15 μl, 20 μl, 25 μl, or 30 μl, were prepared and the quantitative analysis of glycated hemoglobin was performed. Five samples having different glycated hemoglobin concentrations were in turn applied to the six different freeze-dried conjugate structures, and then the levels of glycated hemoglobin were measured. Table 3 below shows the glycated hemoglobin values of the samples and the measured values from the respective freeze-dried conjugate structures applied thereto. Also, the resulting plot is shown in FIG. 7.

TABLE 3

Glycated hemoglobin measurement values according to
the volume of the drop of a freeze-dried conjugate

| HbA1c % | 5 μl | 10 μl | 15 μl | 20 μl | 25 μl | 30 μl |
|---|---|---|---|---|---|---|
| 5.4% | 0.7245 | 0.7845 | 0.8241 | 0.8716 | 0.8944 | 0.9123 |
| 7.2% | 0.8124 | 0.8874 | 0.9214 | 0.96748 | 0.9541 | 1.001 |
| 9.5% | 0.9841 | 1.015 | 1.0135 | 1.09534 | 1.1121 | 1.1231 |
| 11.4% | 1.0245 | 1.1112 | 1.1231 | 1.18901 | 1.2234 | 1.2234 |
| 13.8% | 1.0844 | 1.1945 | 1.2121 | 1.2752 | 1.2955 | 1.3454 |

As can be seen in Table 3 and FIG. 7, in a freeze-dried conjugate structure made with drops having a uniform volume, there was a high degree of linear correlation between the glycated hemoglobin concentration and the glycated hemoglobin values. It was also confirmed through the test that in samples at the same concentration level, the glycated hemoglobin values slightly increases as the volume of the drops of the freeze-dried conjugate increases. The results show that the use of a freeze-dried conjugate structure made with drops having a uniform volume between 5-30 μl helps enhance the accuracy and reproducibility of the quantitative analysis of an immunoassay kit, thereby allowing more accurate qualitative and quantitative assays.

Meanwhile, it was also found that in a freeze-dried conjugate structure made with drops having different volumes, the intensity of the signal may be affected not only by the concentration of glycated hemoglobin in samples, but even by the volume of the drops of the freeze-dried conjugate. For example, a sample having a glycated hemoglobin concentration of 11.4% showed a glycated hemoglobin value of 1.1231 when a freeze-dried conjugate structure having a volume of 15 μl was employed, and the same glycated hemoglobin value (1.1231) was obtained in a sample having a glycated hemoglobin concentration of 9.5% employing a freeze-dried conjugate structure having a volume of 30 μl. This suggests that if a freeze-dried conjugate structure is made with drops having different volumes, the accuracy of sample analysis cannot be guaranteed because it is unclear from what samples measurement values were obtained. This further suggests that the accuracy and reproducibility of the quantitative analysis may be reduced if a freeze-dried conjugate structure made with drops having different volumes is employed.

The invention claimed is:

1. An immunoassay kit comprising:
  (i) a freeze-dried conjugate structure for immunochromatography provided in a chamber comprising a cap, the freeze-dried conjugate structure comprising a first conjugate comprising a first label for signal detection and a first ligand that reacts with an analyte, wherein the first label and the first ligand are physically or chemically linked to each other,
  wherein the freeze-dried conjugate structure is formed by rapidly freezing a dispersion of the first conjugate at a predetermined concentration in a solvent, the dispersion being in the form of drops having a uniform volume of from 5 to 30 μl and a diameter of from 0.5 to 5 mm, followed by freeze-drying, thereby removing the solvent, wherein a space occupied by the solvent in the freeze-dried drops forms a porous space by removing the solvent; and
  (ii) an immunochromatographic strip.

2. The immunoassay kit of claim 1, further comprising a second conjugate comprising a second label for signal detection and a second ligand that reacts with a reporter molecule, in which the second label and the second ligand are physically or chemically linked to each other, and the second label is the same as or different from the first label.

3. The immunoassay kit of claim 1, wherein the ligand is an antigen, an antibody, a receptor or a ligand of the receptor.

4. The immunoassay kit of claim 1, wherein the conjugate structure has a porosity of 70-90%.

5. The immunoassay kit of claim 1, further comprising a buffer for dissolving the freeze-dried conjugate structure.

6. The immunoassay kit of claim 5, wherein the buffer functions to dilute a sample or lyse blood cells.

7. The immunoassay kit of claim 1, further comprising a freeze-dried conjugate structure comprising a second conjugate comprising a second label for signal detection and a second ligand that reacts with a reporter molecule, wherein the second label and the second ligand are physically or chemically linked to each other, and the conjugate structure is formed by rapidly freezing a dispersion, in which the second conjugate is dispersed in a solvent, in the form of drops having a uniform volume, followed by freeze-drying, thereby removing the solvent, wherein a space occupied by the solvent in the freeze-dried drops forms a porous space by removing the solvent.

8. The immunoassay kit of claim 1, wherein the immunochromatographic strip comprises a porous membrane pad, which has formed thereon a test line for capturing an analyte in a sample, and an absorbent pad which is provided at one end of the porous membrane pad and serves to provide a driving force for transferring the analyte.

9. The immunoassay kit of claim 8, wherein the immunochromatographic strip further comprises an underlying solid backing plate.

10. The immunoassay kit of claim 8, wherein the immunochromatographic strip is mounted in a case unit comprising an upper case and a lower case, in which the lower case comprises a guide and a strip support portion, and the upper case comprises a sample introduction port and an observation window at a position corresponding to the test line.

11. The immunoassay kit of claim 8, wherein the test line has immobilized thereon a third ligand that binds specifically to the analyte in the sample.

12. The immunoassay kit of claim 11, wherein the analyte bound to the first label by the first ligand is captured by the third ligand on the test line, and the presence, amount, or both, of the analyte in the sample is determined by measuring a signal generated from the first label on the test line.

13. The immunoassay kit of claim 8, wherein the immunochromatographic strip further comprises, before or after the test line, a control line for determining whether the sample migrated, in which the control line has immobilized thereon a reporter molecule.

14. A method for qualitatively or quantitatively analyzing an analyte in a sample, the method comprising:

adding a buffer solution to a freeze-dried conjugate structure in a chamber to form a uniform dispersion, the conjugate structure comprising a first conjugate comprising a first label for signal detection and a first ligand that reacts with an analyte, wherein the first label and the first ligand are physically or chemically linked to each other, wherein the conjugate structure is formed by rapidly freezing a dispersion of the conjugate structure dispersed in a solvent at a predetermined concentration, the dispersion being in the form of drops having a uniform volume of from 5 to 30 µl and a diameter of from 0.5 to 5 mm, followed by freeze-drying, thereby removing the solvent, adding the sample to the buffer solution containing the uniform dispersion of the freeze-dried conjugate structure and forming a uniform mixture, allowing the mixture to react for a predetermined period of time, loading the mixture from the preceding step onto an immunochromatographic strip and allowing the loaded mixture to migrate along the strip; and determining the presence or absence and intensity of a signal generated from the first label on a test line located on a porous membrane pad of the immunochromatographic strip, thereby qualitatively or quantitatively analyzing the analyte in the sample.

15. The method of claim 14, wherein the sample is whole blood, serum or plasma, and the analyte is glycated hemoglobin.

16. The method of claim 14, wherein the step of rapidly freezing the dispersion is performed by adding the dispersion dropwise to a liquid having an evaporation point between −270° C. and −180° C.

17. The method of claim 16, wherein the liquid is liquid nitrogen or liquid helium.

18. The method of claim 14, wherein the step of rapidly freezing the dispersion is performed by adding the drops having a uniform volume into extremely-low-temperature liquid refrigerant using a dispenser.

* * * * *